(12) United States Patent
O'Lenick et al.

(10) Patent No.: US 8,916,721 B1
(45) Date of Patent: Dec. 23, 2014

(54) PARTITION COEFFICIENT ESTER COMPOSITIONS

(75) Inventors: Thomas G. O'Lenick, Dacula, GA (US); Christopher J. Tarletsky, Stewartsville, NJ (US)

(73) Assignee: SurfaTech Corporation, Lawrenceville, GA (US)

( * ) Notice: Subject to any disclaimer, the term of this patent is extended or adjusted under 35 U.S.C. 154(b) by 266 days.

(21) Appl. No.: 13/507,230

(22) Filed: Jun. 15, 2012

(51) Int. Cl.
*C07C 67/03* (2006.01)
*A61Q 19/00* (2006.01)

(52) U.S. Cl.
CPC ............... *C07C 67/03* (2013.01); *A61Q 19/00* (2013.01); *Y10S 514/887* (2013.01); *Y10S 514/88* (2013.01)
USPC ........... 554/167; 554/227; 514/887; 514/880; 514/506

(58) Field of Classification Search
None
See application file for complete search history.

(56) References Cited

U.S. PATENT DOCUMENTS

| | | | |
|---|---|---|---|
| 6,180,668 B1 * | 1/2001 | O'Lenick et al. | 514/547 |
| 6,605,452 B1 * | 8/2003 | Basheer | 435/134 |
| 8,551,743 B2 * | 10/2013 | Basheer | 435/134 |
| 2004/0037859 A1 * | 2/2004 | Cecchi et al. | 424/401 |
| 2010/0035312 A1 * | 2/2010 | Basheer | 435/134 |

FOREIGN PATENT DOCUMENTS

EP  0910955 A2 *  4/1999  ............... A23D 9/00

OTHER PUBLICATIONS

Koonce, S., et al., A study of alcohols of carnauba wax, Aug. 1944, Oil & Soap, pp. 231-234.*

* cited by examiner

*Primary Examiner* — Yate K Cutliff

(57) ABSTRACT

The present invention is directed to ester compositions which result from the trans-esterification of a triglyceride having an iodine value of between 85 and 175 mg KOH/gm with a fatty alcohol having a melting point of between 35° and 75° C., followed by cooling and removal of the polar phase which results. Surprisingly, we have found the composition has unique properties when used in cosmetic applications.

16 Claims, No Drawings

PARTITION COEFFICIENT ESTER COMPOSITIONS

RELATED APPLICATION

FEDERAL SPONSORSHIP

None

FIELD OF THE INVENTION

The present invention is directed to ester compositions which result from the trans-esterification of a triglyceride having an iodine value of between 75 and 195 mg KOH/gm with a fatty alcohol having a melting point of between 35° and 75° C., followed by cooling and removal of the polar phase which results. Surprisingly, we have found the composition has unique properties when used in cosmetic applications. The fact that the reaction results in a complex mixture, which settles with time and is separated into a semisolid composition of the present invention and a discarded polar phase, gives a unique partition coefficient matched composition. By partition coefficient matched composition is meant a homogeneous, clear when heated above the melt point composition made up of compounds mutually soluble in each other.

DESCRIPTION OF THE ART PRACTICES

Fatty acid esters have been used in the personal care market for many years. They are made by reacting fatty acids with fatty alcohols. The result is fatty ester and water, which is distilled off.

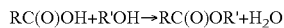

The reaction is run with the objective of making the most pure ester possible. The removal of the water using vacuum, drives the reaction and it is not uncommon to see purity of over 95%.

Prior to the present invention, those of ordinary skill in the art of making cosmetic esters were convinced products with little or no remaining reactants resulted in superior formulation performance. We have subsequently found that this assumption teaches away from our finding that specific compositions that are the result of trans-esterification of unsaturated triglycerides in which glycerin, monoglycerides, diglycerides, as well as the desired fatty ester result in a composition which when allowed to settle, yields an insoluble polar liquid phase on the bottom and a soft ester top phase that when used as a cosmetic ester has unique properties.

Without wanting to be bound by a particular theory, the cooling and settling process results in a composition of solid and liquid compounds, comingled in a buttery matrix, having similar enough polarity to allow miscibility, while expelling more polar materials which wind up in the lower phase upon cooling. We have dubbed this type of composition Partition Coefficient Compositions (PCC), since it is that factor which determines what will and will not remain in the mixture. These compositions have unique spreadability, emmoliency and compatibility with the human skin. We believe it is because the oils on the skin are likewise compositions, which are present on the skin because they have similar partition coefficients. This concept of matching partition coefficients of the oils produced using our process with that of the skin results in unique cosmetic products.

THE INVENTION

Objective of the Invention

It is an object of the present invention to provide a composition of related esters that provide are soluble in each other and have a soft buttery consistency, suitable for use on skin as soft emollient conditioning esters.

SUMMARY OF THE INVENTION

The present invention deals with ester compositions made by the trans-esterification reaction of a solid fatty alcohol, (i.e. one that has a melting point of between 35° C. and 75° C.) with a triglyceride having a iodine value of between 75 mg KOH/gm and 195 mg KOH/gm and optionally a catalyst, forming a mixture of unreacted triglyceride, monoglyceride, diglyceride, glycerin and unsaturated ester of the triglyceride reacted with the solid fatty alcohol. The composition is then cooled to 25° C., whereupon the polar components (namely glycerin and monoglyceride) settle to the bottom of the composition. These polar components are removed from the supernatant yielding a lipophillic composition, which is a soft solid.

An additional aspect of the present invention deals with a process for treating skin by applying to the skin an effective conditioning concentration of an ester compositions made by the trans-esterification reaction of a solid fatty alcohol, (i.e. one that has a melting point of between 35° C. and 75° C.) with a triglyceride having a iodine value of between 85 mg KOH/gm and 175 mg KOH/gm and optionally a catalyst, forming a mixture of unreacted triglyceride, monoglyceride, diglyceride, glycerin and unsaturated ester of the triglyceride reacted with the solid fatty alcohol. The composition is then cooled to 25° C., whereupon the polar components (namely glycerin and monoglyceride) settle to the bottom of the composition. These polar components are removed from the supernatant yielding a lipophillic composition, which is a soft solid.

In a preferred embodiment, the effective conditioning concentration ranges from 0.1% to 25% by weight.

In a more preferred embodiment, the effective conditioning concentration ranges from 1% to 15% by weight.

In order to understand the composition of the present invention one must understand the chemistry of the trans-esterification reaction. This reaction is quite different from the esterification in many respects. Firstly, the reactants, the trans-esterification reaction reacts a triglyceride with an alcohol, whilst the esterification reacts a fatty acid with a fatty alcohol, secondly, the reactants, the trans-esterification reaction results in a number of products of differing polarity (partition coefficient), whilst the esterification reaction results in the desired ester only. Thirdly, the reaction temperature for trans-esterification is lower ranging from 150-160 C whilst the esterification ranges from 170-200° C. This has implications on color, odor and performance. Finally, the trans-esterification reaction can be run without catalyst, which results in a sustainable product that can be certified as ECCOCERT, whilst the esterification process requires catalysts, often tin catalysts.

(A) Raw Materials

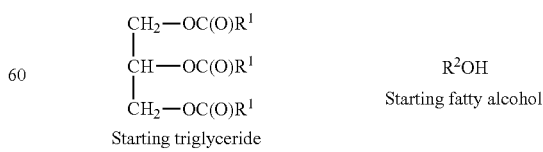

The concentration of the starting triglyceride in the final composition after removal of the polar phase ranges from 1-5% by weight.

$R^1$ is at least 50% by weight C18 unsaturated selected from the group consisting of oleyl and linoleyl;
$R^2$ is saturated alkyl having 13 to 23 carbon atoms.
The concentration of the starting alcohol after removal of the polar phase ranges from 1-10% by weight.

Partially Reacted Products

Monoglyceride

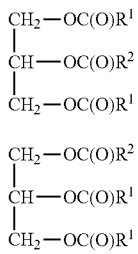

Monoglyceride 1

Monoglyceride 2

$R^1$ is at least 50% by weight C18 unsaturated selected from the group consisting of oleyl and linoleyl.
$R^2$ is saturated alkyl having 13 to 23 carbon atoms.
These are formed in a 1:2 ratio of monoglyceride 1 to monoglyceride 2.
The concentration of this component after removal of the polar phase ranges from 0-5% by weight.

Diglyceride

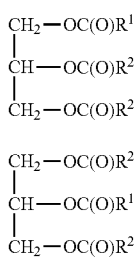

Diglyceride 1

Diglyceride 2

$R^1$ is at least 50% by weight C18 unsaturated selected from the group consisting of oleyl and linoleyl.
$R^2$ is saturated alkyl having 13 to 23 carbon atoms.
The concentration of this component after removal of the polar phase ranges from 5-15% by weight.

Fully Reacted Products

$R^1$ is at least 50% by weight C18 unsaturated selected from the group consisting of oleyl and linoleyl.
$R^2$ is saturated alkyl having 13 to 23 carbon atoms.
This is the predominant product. The concentration of this component after removal of the polar phase ranges from 60-89% by weight.

Co-Product Glycerin.

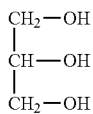

The concentration of this component after removal of the polar phase ranges from 0-5% by weight.

$R^1$ is at least 50% by weight C18 unsaturated selected from the group consisting of oleyl and linoleyl.
$R^2$ is saturated alkyl having 13 to 23 carbon atoms.

It is important to understand that oleyl conforms to the structure $CH_3(CH_2)_7$—CH=CH—$(CH_2)_8$— and linoleyl conforms to the following structure $CH_3(CH_2)_4$—CH=CH—$CH_2$—CH=CH—$(CH_2)_8$—, both are C18 unsaturated cis groups, oleyl substituted at 9 position and linoleyl at the 9 and 12 position. It is this critical structure that disrupts the crystallinity of the resulting composition and gives the unique properties. Likewise the solid crystalline nature of the $R^2$ group is needed for functionality in each of the components of the composition to function.

After the reaction is complete, the reaction mass becomes cloudy, due to the presence of glycerin. The glycerin, generated during the reaction is too polar to be soluble in the diglyceride, triglyceride and desired ester. Consequently upon ceasing mixing, it rapidly separates into a lower layer. As the composition cools, it solidifies, resulting in an easy extraction of the glycerin and polar components soluble in the glycerin. This upper layer solid layer contains the various diglycerides (semisolid), triglycerides (liquid) and the desired product (solid). When heated it exhibits a melt point having a range of about 5° C. and is clear when above its melt point. This clarity of product is indeed verification of the fact that the components contained therein have a compatible partition coefficient as demonstrated by the clarity of the phase and as contrasted with the haze present before separation. The glycerin phase, containing the majority of the monoglycerides is likewise clear when removed, again showing similar partition coefficient of the components of the composition.

The process as defined in the current invention is therefore self cleaning, easy to practice, and results in a unique product composition, as will be disclosed subsequently, the composition contains (a) solid plate like crystals (the fully reacted product), (b) a semisolid amphorus material (the diesters) and a liquid product (triglyceride). Photomicrographs show that the composition has (a) a highly structured solid matrix (b), an amphorous phase distributed therein and (c) a liquid phase dispersed evenly therein. The phases match up the letters above.

Surprisingly, the compositions of the present invention have unique and heretofore unappreciated advantages over more traditional methods, vis-à-vis cosmetic properties, including spread, skin feel and emollient properties.

It is also an important part of the present invention that natural triglycerides be used as raw materials for the preparation of the compositions of the present invention Naturally occurring triglycerides do not have a singly fatty component, but have a distribution of fatty acids selected by nature and evolution of the plant over many years. This natural composition, in part is responsible for unique skin properties observed when one uses the composition of the present invention on skin, in either a serum or an emulsion.

The compositions of the present invention when applied to skin have outstanding spread profiles, absorption rates and conditioning properties offering heretofore unavailable alternative compounds to traditional synthetic non-polar compounds such as Petroleum, silicone and synthetic compounds used in topically applied products in the form of O/W, W/O and anhydrous.

The products produced by the process of the present invention is directly responsible for the, surprising and unexpected, effects including but not limited to spread profiles, absorption rates and conditioning properties to the skin and hair spread profile in combination with the target ester compound, wherein, if just a simple esterification process were utilized the effect would not be observed. For example a simple esterification of stearyl alcohol and oleic acid to form, Stearyl Oleate, would not contain the spread and absorption profile of a Stearyl oleate obtained from the reaction of Stearyl Alcohol and Olive oil that contains the described acid composition in the second paragraph above. Utilizing these natural oils as described in paragraph two above allows for this effect to be noticed, which is driven by the trans-esterification process.

DETAILED DESCRIPTION OF THE INVENTION

The present invention discloses an ester compositions made by the trans-esterification reaction of
(a) a solid fatty alcohol, having a melting point of between 35° C. and 75° C.;
(b) with a triglyceride having a iodine value of between 75 and 195 mg KOH/gm and
(c) optionally a catalyst,
forming a mixture of unreacted triglyceride, monoglyceride, diglyceride, glycerin and unsaturated ester of the triglyceride reacted with the solid fatty alcohol;
said trans-esterification conducted at as temperature of 150-200° C. for 4 to 10 hours;
said composition is allowed to cool without agitation to 25° C., over a period of at least 30 minutes,
whereupon a top solid layer forms and a bottom liquid layer forms;
finally, the bottom layer is removed from the mixture by resulting in
a lipophillic composition of the present invention.

In a preferred embodiment the fatty alcohol has a melt point of between 40 and 60° C.

In a preferred embodiment the fatty alcohol has a melt point of between 35 and 50° C.

In a preferred embodiment the fatty alcohol has a melt point of between 50 and 75° C.

In a preferred embodiment the iodine value of the triglyceride ranges from 85-95 mg KOH/gm.

In another preferred embodiment the iodine value of the triglyceride ranges from 100-175 mg KOH/gm.

In a preferred embodiment the reaction is conducted with no catalyst.

In a preferred embodiment the reaction is conducted with between around 0.1 and 0.3% by weight stannous oxylate.

In a preferred embodiment said trans-esterification is conducted at as temperature of 150-170° C. for 4 to 10 hours.

In a preferred embodiment said trans-esterification is conducted at as temperature of 150-170° C. for 7 to 10 hours.

In a preferred embodiment the composition is allowed to cool without agitation to 25° C., over a period of at least 60 minutes, In a preferred embodiment the bottom layer is removed from the mixture by simply opening the valve at the bottom of the vessel.

Additionally, the invention is directed to a trans-ester composition comprising:
(a) between 1-5% by weight of;

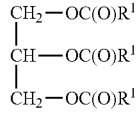

(B) between 1-10% by weight of;

(C) between 0-5% by weight of a mixture of monoglycerides conforming to the following structure:

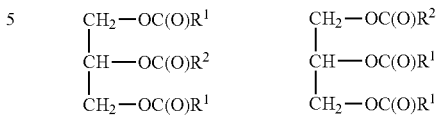

(D) between 5-15% by weight of a mixture of diglycerides conforming to the following structure:

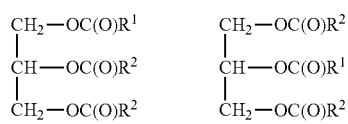

between 60-89% by weigh an ester conforming to the following structure:

and
between 0-5% by weight of glycerin conforming to the following structure:

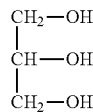

wherein;
$R^1$ is at least 50% by weight C18 unsaturated selected from the group consisting of oleyl and linoleyl.
$R^2$ is saturated alkyl having 13 to 23 carbon atoms.

An additional aspect of the present invention deals with a process for treating skin by applying to the skin an effective conditioning concentration of an ester compositions made by the trans-esterification reaction of a solid fatty alcohol, (i.e. one that has a melting point of between 35° C. and 75° C.) with a triglyceride having a iodine value of between 85 mg KOH/gm and 175 mg KOH/gm and optionally a catalyst, forming a mixture of unreacted triglyceride, monoglyceride, diglyceride, glycerin and unsaturated ester of the triglyceride reacted with the solid fatty alcohol. The composition is then cooled to 25° C., whereupon the polar components (namely glycerin and monoglyceride) settle to the bottom of the composition. These polar components are removed from the supernatant yielding a lipophillic composition, which is a soft solid.

In a preferred embodiment, the effective conditioning concentration ranges from 0.1% to 25% by weight.

In a preferred embodiment, the effective conditioning concentration ranges from 1% to 20% by weight.

In a more preferred embodiment, the effective conditioning concentration ranges from 10% to 15% by weight.

In a preferred embodiment the process for conditioning skin is delivered in a serum.

In a preferred embodiment the process for conditioning skin is delivered in a emulsion.

Hair and skin are made up of protein. Protein in turn is composed of amino acids, which are assembled into what is referred to as primary structure. The peptide bond as it is referred to by biochemists is referred to as polyamides by organic chemists. The amino acid structure has a secondary structure which relates to hydrogen bonding, giving each protein a three dimensional structure. There are also disulfide bonds between sulfur bearing amino acids. For the most part, unless you are relaxing or perming hair you do not want to do anything to alter the protein structure.

Additionally, hair and skin contain oils. The build up of which constitutes the major portion of what is commonly called "soils". Some of these materials are superficial and can be easily removed while others soils are located deeply within the hair and skin and are not easily removed. An understanding of these materials and how they function is critical to understanding healthy hair and skin.

A key article related to this analysis is entitled Hair Lipids and their contribution to perception of hair oiliness. Koch, J. et al, Hair Lipids and their contribution to perception of hair oiliness, J. Soc. Cosmet. Chem. 33, 317-326, November 1982.

The Koch article defines two types of oils, the first referred to as "external oiliness" and the second as "internal oiliness". The article points out that some of the oil that designated external oil is superficial and needs to be removed in cleaning. The remainder of the oil remains strongly absorbed onto the hair and in the cuticle and can only be removed by strong extraction. It has been shown by consumer testing that the internal oil does not contribute to the consumer perception of oiliness on hair or skin. It does however function as what Koch calls a "storage capacity" for oil. This is important because the internal oil works its way to the surface, replenishing the oils fund in the natural state. This mechanism explains why hair and skin become oily even when washed on a quite regularly basis. Healthy hair and skin have oil present on them.

Koch also points out that the nature of the oil and not only its concentration has a major effect upon the consumer perception of oiliness both on hair and on skin.

We have found that the topical application of the compounds of the present invention to cleaned skin and hair results in a more rapid re-establishment of the natural balance of the internal oils of the hair and skin. When the ester is applied to the hair or skin as taught in our process, effects the speed in which the healthy internal oil composition is achieved on the hair or skin. The oil spreading from the internal oil storage, results in a highly desirable feel on the hair and skin as it is perceived by the consumer.

The oils observed on the hair vary considerably in terms of polarity. If the extraction of oils is not the same based upon this difference in polarity, the extracted oils will not be the same as those removed by shampooing. Koch developed extraction methodologies that both showed the composition of internal and external oils and related directly to those extracted by detergents. This outstanding analytical work has allowed for both structure elucidation and quantification of the components of both internal and external oils. The methodology finds both non-polar oils like triglycerides, and far more polar components like mono acyl glycerides commonly found on the hair and skin. Since these classes of compounds differ appreciably in polarity, an extraction of external oils must pick the polar and non-polar oils from the hair and leave the internal oils in tact. It was determined in the Koch reference that the best extraction solvent for the polar and non-polar oils on the hair as external oils is a mixture of water and chloroform. The presence of water has a profound effect upon cleaning hair. Water swells the hair during shampooing, which is thought to have an impact on the availability of the internal oiliness especially just under the cuticle. The object of the experiment of Koch et al was to identify the external oils extracted from the hair during cleansing.

It was determined that the "average commercial shampoo" removes 40-60% of the total oils in the hair. This quantity matches up well with the extraction method of Koch. The internal oils are extracted using extreme methods, specifically, the extractions conducted by Soxhlet extractions with boiling ether and water for 16 hours.

The composition of the oils removed by detergents is called "external oils".

|  | External | |
|---|---|---|
|  | mg extracted | % Comp |
| Squalene | 0.26 | 9.4 |
| Cholesterol Esters | 0.56 | 20.3 |
| Triglycerides | 0.51 | 18.5 |
| Free Fatty Acid | 1.27 | 46.0 |
| Cholesterol | 0.05 | 1.8 |
| Monoglycerides | 0.11 | 4.0 |
| Total | 2.76 | 100.0 |

The composition of oils are not removed by detergents is the so called "Internal oils".

Composition of Internal Oils

|  | Internal | |
|---|---|---|
|  | mg extracted | % Comp |
| Squalene | 0.31 | 30.4 |
| Cholesterol Esters | 0.11 | 10.8 |
| Triglycerides | 0.12 | 11.8 |
| Free Fatty Acid | 0.15 | 14.7 |
| Cholesterol | 0.21 | 20.6 |
| Monoglycerides | 0.12 | 11.8 |
| Total | 1.02 | 100.0 |

The fact that the composition of internal oil and external oil is not identical indicates there is some preferential absorption of compounds rich in internal oil but lean in the external oil. In short the hair and skin "dump" the less desirable oils out of the structure.

Comparison of External Oils v. Internal Oil Location

|  | External | Internal | Total | % Internal | % External |
|---|---|---|---|---|---|
| Squalene | 0.26 | 0.31 | 0.57 | 54.4 | 45.6 |
| Cholesterol Esters | 0.56 | 0.11 | 0.67 | 16.4 | 83.6 |
| Triglycerides | 0.51 | 0.12 | 0.63 | 19.0 | 81.0 |
| Free Fatty Acid | 1.27 | 0.15 | 1.42 | 10.6 | 89.4 |
| Cholesterol | 0.05 | 0.21 | 0.26 | 80.8 | 19.2 |
| Monoglycerides | 0.11 | 0.12 | 0.23 | 52.2 | 47.8 |
|  | 2.76 | 1.02 | 3.78 | — | — |

Difference in Oils by Location. Internal to External Ratio

|  | % Internal | % External | I:E Ratio |
|---|---|---|---|
| Squalene | 54.4 | 45.6 | 1.2 |
| Cholesterol Esters | 16.4 | 83.6 | 0.2 |
| Triglycerides | 19.0 | 81.0 | 0.2 |
| Free Fatty Acid | 10.6 | 89.4 | 0.1 |
| Cholesterol | 80.8 | 19.2 | 4.2 |
| Monoglycerides | 52.2 | 47.8 | 1.1 |

High I:E ratios indicate a component that is held within the hair and does not readily pass to the outside. Cholesterol Esters are strongly retained on the inside by a 4.2:1 ratio. Monoglycerides and Squalene are roughly equal showing little preference for internal or external. Free fatty acids, triglycerides and cholesterol esters favor the external phase.

We have determined that when the esters of the present invention are applied to the hair after cleansing, there is initially a repair of the cuticle. The application of our ester does not effect the trans epidermal water loss, which is the coating is non-occlusive. This allows water to pass from inside to out and allows for a more rapid equilibrium of internal oil to the surface of the hair or skin that has been denuded of external oils. Prior to the present invention, large amounts of oils and quaternary compounds were applied after washing to minimize damage. Our methodology allows the oils that are in the skin and hair to come out making a natural conditioning.

The efficient and expeditious establishment of the equilibrium of oils within the hair and skin and those on the outside results in cosmetically elegant appearance, healthy balance and natural equilibrium.

The traditional treatment methods using fatty quaternaries, fatty alcohols, mineral oils and the like all result in a hair and skin having materials that are not normally present on hair or skin and are in fact materials that need to be removed in the next wash. This is seen as greasiness on skin or build up on hair.

Raw Materials Fatty Alcohol

Examples 1-15

The compounds used as raw materials are available from a variety of sources including Sasssol in Germany. The following are examples

| | | | Example | | | | |
|---|---|---|---|---|---|---|---|
| Name | Common Name | CAS | Form | MW | OH Val | MP | Bp |
| 1-Tridecanol | | 112-70-9 | $C_{13}H_{28}O$ | 200.4 | 280 | 30 | 276 |
| 1-Tetradecanol | mristyl alcyohol | 112-72-1 | $C_{14}H_{30}O$ | 214.4 | 261 | 38 | 172 (2.67) |
| 1-Pentadecanol | | 629-76-5 | $C_{15}H_{32}O$ | 228.4 | 245 | 44 | |
| 1-Hexadecanol | cetyl alcohol | 36653-82-4 | $C_{16}H_{34}O$ | 242.5 | 230 | 49 | 194 |
| 1-Heptadecanol | margaryl alcohol | 1454-85-9 | $C_{17}H_{36}O$ | 256.5 | 218 | 54 | |
| 1-Octadecanol | stearyl alcohol | 112-92-5 | $C_{18}H_{38}O$ | 270.5 | 207 | 58 | 214 (2.67) |
| 1-Nonadecanol | | 1454-84 | $C_{19}H_{40}O$ | 284.5 | 196 | 62 | |
| 1-Eicosanol | arachidyl alcohol | 629-96-9 | $C_{20}H_{42}O$ | 298.6 | 187 | 64 | 215 (1.33) |
| 1-Heneicosanol | | 15594-90-8 | $C_{21}H_{44}O$ | 312.6 | 179 | 68 | |
| 1-Docosanol | behenyl alcohol | 661-19-5 | $C_{22}H_{46}O$ | 326.6 | 171 | 71 | 241 (1.33) |
| 1-Tricosanol | | 3133-01-5 | $C_{23}H_{48}O$ | 340.6 | 164 | 74 | |

| Example | Description |
|---|---|
| 12 | A blend of Eicosanol (50% by Weight) and Tridecanol (50% by Weight) |
| 13 | A blend of Tricosanol (50% by Weight) and Octadecanol (50% by Weight) |
| 14 | A blend of Eicosanol (50% by Weight) and Pentadecanol (50% by Weight) |
| 15 | A blend of Pentadecanol (50% by Weight) and Tridecanol (50% by Weight) |

In the above chart, CAS stands for chemical abstract number;
MW stands for molecular weight in grams/mole
OH Val stands for hydroxyl value in mg KOH/gm
MP stands for melting point in degrees C.
and Bp stands for boiling point in degrees C.

Example 17 Stannous Oxylate

Stannous oxylate is a well known catalyst and is an item of commerce having a CAS number 814-94-8. It has the following structure:

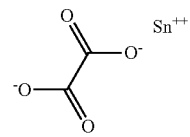

Raw Materials Triglyceride

Example 18-40

The natural oils useful as raw materials in the preparation of the compounds of the present invention are available from a variety of sources including Arista.

Example 18

Crambe Oil (*Crambe abyssinica*)

Crambe oil is an oilseed crop from the mustard family, which includes crops such as rapeseed (canola and industrial rapeseed oil) and tame mustard.
CAS Number: 68956-68-3
EINECS Number: 273-3,3-5
Iodine Value: 88

Example 19

Apricot Kernel Oil (*Prunus armeniaca*)

Apricot Kernel oil is a triglyceride extracted from the kernel of *Prunus armeniaca*.
CAS Number 72869-69-3
EINECS Number: 272-046-1
Iodine Value: 102
Titer Point: 43° C.
C18 unsaturated: 52%

Example 20

Mango Butter (*Mangifera indica*)

Mango Butter is a butter derived from *Mangifera indica*. It comes from the India. It is said to be a good skin emollient.
CAS Number: 167747-3606
Iodine Value: 120

Example 21

Avocado Oil (*Persea gratissima*)

Avocado oil is a triglyceride coming from the pressing of the dehydrated fruit of the avocado (*Persea grantissima*). The pulp of the fruit has a great deal of oil present (70% by weight).
CAS Number: 8024-32-6 EINECS Number: 232-274-4
Iodine Value: 85

Example 22

Cottonseed Oil (*Gossypium*)

Cottonseed is a triglyceride derived from cotton (*Gossypium hirsutum*). Cotton, like soybean, is a very important crop, in that the crop has a protein, and fatty component, but unlike soybean, the fiber is very useful in textile applications. Cotton is widely grown and has been known for many years.
CAS Number: 8001-29-4 EINECS Number 232-280-7
Iodine Value: 108

Example 23

Rice Bran Oil (*Oryza sativa*)

Rice Bran oil is a triglyceride extracted from rice. It comes from Japan.
CAS Number: 68553-81-1
EINECS Number: 232-409-7
Iodine Value: 105

Example 24

Wheat Germ Oil (*Triticum vulgare*)

Wheat germ oil is a triglyceride derived from the extraction of wheat germ.
CAS Number: 8046-25-1
Iodine Value: 130

Example 25

Corn Oil (*Zea mays*)

Corn oil is a triglyceride derived from the wet milling of corn (*Zea mais*, Graminae). It is cultivated in all the temperate areas of the world.
CAS Number 8001-30-7
EINECS Number: 232-281-2
Iodine Value: 123

Example 26

Olive Oil (*Olea europaea*)

Olive oil is a triglyceride, which has occupied a unique position in civilization. It is the oldest oil known to man. It is produced throughout the area that was once the Roman Empire.
CAS Number: 8001-25-0
EINECS Number: 232-277-0
Iodine Value: 85

Example 27

Poppy Seed Oil (*Populus nigra*)

Poppy seed oil is a triglyceride derived from the poppy (*Papaver orientiale*). It was originally cultivated in Asia Minor, but is now produced in Europe.
CAS Number: 8002-11-7
Iodine Value: 138

Example 28

Grape Seed Oil (*Vitis vinifera*)

Grapeseed oil is a triglyceride derived from grape (*Vitis Vinifera*). It is cultivated in many areas of the world, but originated in the Mediterranean coast (Italy, France, Turkey, Greece and Yugoslavia).
CAS Number: 8024-22-4
EINECS 287-896-9
Iodine Value: 135

Example 29

Sesame Oil (*Sesamum indicum*)

Sesame oil is a triglyceride, which is derived from *Sesamun indicum*. It is cultivated in Africa, Europe, China, Central and South America and the southern U.S. It is one of the world's oldest crops.
CAS Number: 8008-74-0
EINECS Number: 232-370-6
Iodine Value: 110

Example 30

Sweet Almond Oil (*Prunus amygdalus* dulcis)

Sweet almond oil is a triglyceride derived from the almond (*Prunus amygdalus*). It is cultivated in all the temperate areas of the world.
CAS Number: 8007-69-0
EINECS: 291-061-4
Iodine Value: 102

Example 31

Hazelnut Oil (*Corylus americana*)

Hazelnut oil is a triglyceride derived from the nut of the hazelnut tree (*Corylus avellana*). It is cultivated in Europe, principally Italy, Spain and Turkey. Hazelnut oil contains natural preservatives and antioxidants, which render the oil very stable.
CAS Number: 84012-21-5
EINECS Number: 281-667-7
Iodine Value: 86

Example 32

Soybean oil (*Glycine soja*)

Soybean oil is a triglyceride derived from the soybean (Glycerin max L). The soybean originated in China, as far back as 2,300 BC. It was later widely cultivated in North America, most importantly in the U.S., where it is a major food crop.
CAS Number: 8001-22-7
EINECS Number: 232-274-4
Iodine Value: 130

Example 33

Safflower Oil

Safflower oil is a triglyceride derived from the species *Carthamus Tinctorius*. It originates in the Orient, but the U.S. production has been selected to maximize the polyunsaturate content.
CAS Number: 8001-23-9
EINECS Number: 232-276-6
Iodine Value: 145

Example 34

Hybrid Safflower Oil (*Carthamus Tinctorius*)

Hybrid Safflower oil is a triglyceride derived from the species *Carthamus Tinctorius*. This is the high oleic species. It originates in the Orient, but the U.S. production has been selected to maximize oil content.
CAS Number: 8001-23-8
EINECS Number: 232-276-6
Iodine Value: 140

Example 35

Walnut Oil (*Juglans regia*)

Walnut oil is a triglyceride derived from the walnut (*Juglans regia*). It originated in Persia, and is now cultivated in Europe. Southern France is the major area in which Walnuts are cultivated.
CAS Number: 8024-09-7
EINECS Number: 84604-00-2
Iodine Value: 150

Example 36

Canola Oil (Canola)

Canola oil is a triglyceride produced from genetically modified rapeseed to change the principal fatty acid from C-22 to C-18. It was developed in Canada, it is now widely available throughout the world.
CAS Number: 120962-03-0
EINECS Number: 232-3,3-5
Iodine Value: 92

Example 37

Peanut Oil (*Arachis hypogaea*)

Peanut oil is a triglyceride derived from peanuts (*Arachis hypogea* L.). It is cultivated in many areas of the world, since it is easy to grow.
CAS Number: 8002-03-07
EINECS Number: 232-296-4
Iodine Value: 98

Example 38

Tall Oil (Tallol)

Tall oil is an acid derived from wood, and is the by-product of the wood pulp industry. Crude tall oil contains about 42% rosin acids. Rosin acids are a group of polycyclic carboxylic acids consisting of abietic acid, dihydroabetic acid, neoabetic acid, palustric acid, pimaric acid and iso-pimaric acid. The light fractions of tall oil (heads) consist mainly of palmitoleic acid. The fatty acids found in refined, distilled tall oil (TOFA) are:
CAS Number: 8002-26-4
EINECS Number 232-304-6
Iodine Value 130

Example 39

Kokum Butter (*Garcinia indica*)

Kokum Butter is a butter derived from *Garcinia indica*. It comes from the India. It is said to be a natural emollient and moisturizer, used in hair and skin care.
CAS Number: 8496-02-6
EINECS: 283-622-7
Iodine Value: 131

Example 40

Sunflower Seed Oil (*Helianthus annuus*)

Sunflower seed oil is a triglyceride derived from the seeds of the sunflower (*Helianthus annus* L.). It was originally cultivated in North America by native Indians. It is now cultivated in North America, Russia, Europe South America, India and China. It is a rather common plant.
CAS Number: 8001-21-6
EINECS Number: 232-273-9
Iodine Value: 130

Catalysed Trans Esterification

Examples 41-63

General Procedure

To the specified number of grams of alcohol (examples 1-15) is added the 300 grams of the specified triglyceride (Examples 16-39). Next add 0.1% by weight of stannous oxylate (based upon the total weight added), under good agitation. The temperature of the mass is raised to 160-170 C. for 8 hours, during which time the reaction mass becomes cloudy. The reaction mass is allowed to cool over a period of 1-2 hours. During that time a semisolid top layer forms and a liquid bottom phase form. The bottom phase is removed by draining the glycerin rich lower liquid layer from the solid top layer. Once compete, the solid layer is used without additional purification. It is the components of the top layer that have the desired properties and composition.

Examples 41-63

| Example | Triglyceride Example | Fatty Example | Alcohol Grams |
|---|---|---|---|
| 41 | 18 | 1 | 200 |
| 42 | 19 | 2 | 214 |
| 43 | 20 | 3 | 228 |
| 44 | 21 | 4 | 242 |
| 45 | 22 | 5 | 256 |
| 46 | 23 | 6 | 270 |
| 47 | 24 | 7 | 284 |
| 48 | 25 | 8 | 300 |
| 49 | 26 | 9 | 312 |
| 50 | 27 | 10 | 326 |
| 51 | 28 | 11 | 340 |
| 52 | 29 | 12 | 287 |
| 53 | 30 | 13 | 305 |
| 54 | 31 | 14 | 273 |
| 55 | 32 | 15 | 223 |
| 56 | 33 | 15 | 223 |
| 57 | 34 | 14 | 273 |
| 58 | 35 | 13 | 305 |
| 59 | 36 | 12 | 287 |
| 60 | 37 | 11 | 340 |
| 61 | 38 | 10 | 327 |
| 62 | 39 | 9 | 313 |
| 63 | 40 | 8 | 300 |

Uncatalysed Trans Esterification
General Procedure

To the specified number of grams of alcohol (examples 1-15) is added the 300 grams of the specified triglyceride (Examples 16-39) under good agitation. The temperature of the mass is raised to 160-170 C. for 12 hours, during which time the reaction mass becomes cloudy. The reaction mass is allowed to cool over a period of 1-2 hours. During that time a semisolid top layer forms and a liquid bottom phase form. The bottom phase is removed and the top layer is used without additional purification.

Examples 64-86

Examples 41-63

| Example | Triglyceride Example | Fatty Example | Alcohol Grams |
|---|---|---|---|
| 64 | 18 | 1 | 200 |
| 65 | 19 | 2 | 214 |
| 66 | 20 | 3 | 228 |
| 67 | 21 | 4 | 242 |
| 68 | 22 | 5 | 256 |
| 69 | 23 | 6 | 270 |
| 70 | 24 | 7 | 284 |
| 71 | 25 | 8 | 300 |
| 72 | 26 | 9 | 312 |
| 73 | 27 | 10 | 326 |
| 74 | 28 | 11 | 340 |
| 75 | 29 | 12 | 287 |
| 76 | 30 | 13 | 305 |
| 77 | 31 | 14 | 273 |
| 78 | 32 | 15 | 223 |
| 79 | 33 | 15 | 223 |
| 80 | 34 | 14 | 273 |
| 81 | 35 | 13 | 305 |
| 82 | 36 | 12 | 287 |
| 83 | 37 | 11 | 340 |
| 84 | 38 | 10 | 327 |
| 85 | 39 | 9 | 313 |
| 86 | 40 | 8 | 300 |

The composition of the present invention contains elements that are solid and semisolid at ambient conditions. By altering the type of triglyceride and more importantly the type of alcohol the ratio of the solid to liquid can be altered. This in turn changes the skin feel attributes. More solid makes the wax more resistant to spread (waxy), but provides an occlusive film on the skin. The more the semisolid portion the more the glide the wax has upon application to the skin.

Example 72 is an ester composition comprising:
(a) 2% by weight of;

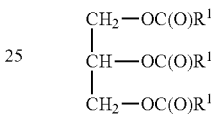

(B) 4% by weight of;

$R^2OH$ (C) 0.5% by weight of a mixture of monoglycerides conforming to the following structure:

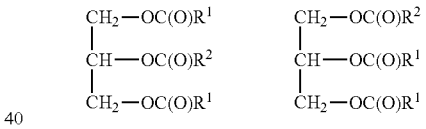

(D) 8% by weight of a mixture of diglycerides conforming to the following structure:

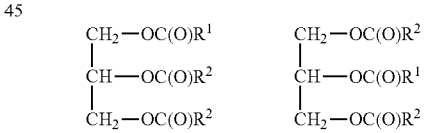

85% by weigh an ester conforming to the following structure;

$R^2OC(O)R^1$ and
0.5% by weight of glycerin conforming to the following structure:

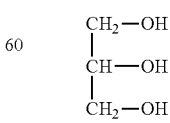

Applications Data

Fats and oils are triacylglycerols separated by the slightly arbitrary distinction of solid or liquid state at room temperature. In triacylglycerols of vegetable origin, fatty acids esterified onto position 2 significantly differ from those esterified onto positions 1 and 3—which exhibit little overall difference in substitution pattern, whereas in products of animal origin random substitution seems to predominate. Even numbered fatty acid moieties, the most abundant ones throughout, tend to show higher solid/liquid transition temperatures due to higher Van der Waals interactions per unit weight. Saturated fatty acid residues tend to adopt mainly a zigzag type of conformation when in the crystal lattice of triacylglycerols, and the inclusion of a trans double bond does not significantly affect this situation, despite the slight shortening of the carbon chain, which it entails. The existence of a cis double bond introduces a bending of the chain, and lowers transition temperatures. Much the same situation arises in the somewhat simpler situation of fatty acid crystals, themselves, and is illustrated by the relative values of stearic acid (69.6° C.), which is the saturated 18 carbon atom fatty acid often abbreviated as (18:0), which compares with 62.9° C. for palmitic acid (16:0) and only 61.3 for margaric acid (17:0), and also with 13.4° C. for oleic acid (18:1, (9-cis)), and 46° C. for elaidic acid (18:1, (9-trans)). This feature is even stronger when various isolenic cis double bonds are present, as in -linoleic acid (18:2, (9-cis, 12-cis) which melts at −5° C. and -linolenic acid (18:3, (9-cis, 12-cis, 15-cis)), which melts at −11° C. Department of Chemical Engineering, Instituto. Superior Técnico, Lisbon (Portugal), October 1997

Lipids exhibit peculiar melting properties, which form the basis for their selection for a number of uses and underlie apparent physiological selectivity's.

It is of common knowledge that natural fats do not have a perfect distribution of fatty acids among the glyceride molecules. The tendency for certain acids to be more concentrated at particular positions varies according to species and their environment and location in the plant or animal. The physical characteristics of a fat are greatly affected not only by the nature of constituent fatty acids (i.e. chain length and unsaturation) but also, by their distribution in the triacylglycerol molecules. In effect, the unique fatty acid distribution patterns of some natural fats limits their industrial applications. Inter-esterification is one of the processes that can be applied to improve the consistency of such fats and to improve their usefulness. This process involves rearranging the fatty acids in such a way that their distribution among the triacylglycerol molecules of the fat becomes random (random interesterification) or conforms to some special pattern (directed interesterification). Interesterification results when fat is heated at relatively high temperatures (less than 200° C.) for a considerably long period. Nevertheless, catalysts are frequently used that permit a shorter period (30 min.) for the completion of the reaction at temperatures as low as 50° C. Alkali metals and alkali metal alkylates are effective low-temperature catalysts, sodium methoxide ("methylate") being the most commonly used one. Approximately 0.1% catalyst is required. Higher concentrations may cause excessive losses of oil resulting from the formation of soap and methyl esters.

The effect is such that, if the total fat content 20% and higher and:

The LA acid content is between 2.00% and 85.00%
More preferably the LA content is between 2.00 and 50.00%
Most preferably if the LA content is between 2.00% and 30.00%
The LNA content is between 0.100 and 60.00%
More preferably the LNA content is between 0.100 and 30.00%
Most preferably if the LNA content is between 0.100 and 15.00%
The LA+LNA concentration results in the total Polyunsaturated concentration to be between 2.00% and 85.0%
More Preferably the LA+LNA concentration results in the total Polyunsaturated concentration to be between 2.00% and 60.0%
Most preferably the LA+LNA concentration results in the total Polyunsaturated concentration to be between 2.00% and 35.00%

The resulting effect is that the gelling properties spread profiles, absorption rates and conditioning properties to the skin and hair offers ideal alternative compounds to traditional synthetic non-polar compounds such as Petroleum, silicone and synthetic compounds used in topically applied products in the form of O/W, W/O and anhydrous. (please reference the link supplied FAT COMPOSITION) for a listing of the oil types demonstrating this "surprisingly and un-expectedly" effect when esterified.

The fact the products of the current invention are compositions, rather than compounds that drives, surprisingly and unexpectedly, the resulting effect is that the gelling properties spread profiles, absorption rates and conditioning properties to the skin and hair spread profile in combination with the target ester compound, wherein, if just a simple esterification process were utilized the effect would not be observed. For example a simple esterification of Stearyl Alcohol and Oleic acid to form, Stearyl Oleate, would not contain the spread and absorption profile of a Stearyl oleate obtained from the reaction of Stearyl Alcohol and Olive oil that contains the described acid composition in the second paragraph above. Utilizing these natural oils as described in paragraph two above allows for this effect to be noticed, which is driven by the interesterification process.

The results support the development and functional profiles of select these composition of the current invention, rather than pure compounds to deliver comparable spread profiles, absorption profiles, moisturizing and condition properties to skin and hair, versus the simple esterification of one alcohol and one acid.

Formulations

Description of Emulsifiers and Surfactants:

(NONIONIC) Alkoxylated alcohols, or ethers formed by the reaction of alkylene oxide. Monosaccharides and polysaccharides as well as alkoxylated carboxylic acids, alkoxylated sorbitan, fatty acids, fatty alcohols, and sorbitan derivatives. Also, nonionic silicone surfactants which are silicone polymers that contain at least one hydrophilic radical and one lipophilic radical. Some examples of surfactants in combinations used are: Disodium laureth sulfosucinates, sodium acyl isethionate, acyl-betaine, sodium lauryl sulfoacetate, acyl glucosides, sodium acyl sarcosinate, and sodium cocoyl amino acids.

Classification of anionic, cationic and amphoteric surfactants are disclosed in U.S. Pat. No. 5,534,265. Include the surfactants utilized in Body wash study.

Description Viscosity Modifiers;

Natural or synthetic are montmorillonite minerals and quaternized derivatives of such. Polymeric viscosity modifiers described as associative thickeners that generally contain a hydrophilic backbone and a pendant hydrophobic side chain. Silica and silicates and derivative thereof are another type of viscosity modifier. Also, other types of suitable oil viscosity modifiers are waxes or solid materials. A Varity of waxes are suitable including but not limited to, animal, vegetable waxes, which are extracted or saturated.

Oils:

Oils that are defined as liquid at ambient temperature that can be described as esters that are mono, di and triesters. Glyceryl Esters of fatty acids. Oils can also be refined and unrefined natural extracted oils that are predominantly polar.

Film Formers:

The film formers can be water soluble, or water insoluble that deposit on the target substrates of skin and hair and when the intended composition evaporates leaves a film on the substrate. Soluble defined as the film forming polymer will form a single homogenous phase when incorporated into the intended phase.

Active Ingredients:

Described as organic sunscreens defined as UVA, UVB absorbing and sun blocking agents, vitamins, coenzymes, antioxidants, anti-inflammatory and botanical extracts.
Aluminumchlorohydrate Pigments:

Described as Mica, Titanium Dioxide, Zinc Oxide, Iron Oxides, Silicates, Nylon and nylon derivatives, and surface treated derivatives of Titanium Dioxide, Zinc Oxide, Mica and iron oxides.

Preservatives:

Described as benzyl alcohol, benzoic acid, benzylhemiformal, DEDM and others listed in the INCI Cosmetic ingredient handbook.

Humectants:

Described as di, or polyhydric alcohols such as glycols, sugars like glucose, fructose, maltose mannitol, sucrose, and xylose.

Oil in Water Formulation Used:

| INGREDIENTS %/wt | Example | | | |
|---|---|---|---|---|
| | 87 | 88 | 89 | 90 |
| Water | qs | qs | qs | qs |
| Disodium EDTA | 0.05 | 0.05 | 0.05 | 0.05 |
| Glycerin | 5.00 | 5.00 | 5.00 | 5.00 |
| Ethylhexyl Stearate | 10.50 | 10.50 | 10.50 | 10.50 |
| Glyceryl Stearate/PEG 100 Stearate | 2.50 | 2.50 | 2.50 | 2.50 |
| Cetearyl Alcohol/Ceteareth-20 | 3.00 | 3.00 | 3.00 | 3.00 |
| Cetearyl Alcohol | 3.00 | 3.00 | 3.00 | 3.00 |
| Ascrobyl Acetate | 1.00 | 1.00 | 1.00 | 1.00 |
| Preservative | 1.00 | 1.00 | 1.00 | 1.00 |
| Behenyl Olivate | 3.00 | 0.00 | 3.00 | 0.00 |
| Behenyl Behenate | 0.00 | 3.00 | 0.00 | 3.00 |
| Pigments-Iron Oxides | 18.00 | 18.00 | 0.00 | 0.00 |
| PVP Eicosene Copolymer | 0.75 | 0.75 | 0.75 | 0.75 |
| C10-C30 Alkyl Acrylate Crosspolymer | 1.00 | 1.00 | 1.00 | 1.00 |

ESSACHEM Thickener: Behenyl Olivate, Stearyl Olivate, C-36 JARCOL Safflowate, Unilin 425 Olivateate, Behenyl Safflowate, Stearyl Flaxate, Unilin-425 Sunflowate Tested Synthetic Thickener(ESTERS) Myristyl Myristate, Behenyl Behenate, Stearyl Stearate, Myristal Ester of Hydrogenated Olive oil, Hydrogenated castor oil, Carnauba wax, Candeliliia wax, oxokerite, beeswax, synthetic beeswax, lanolin wax, cetyl alcohol, stearyl alcohol.

Oil-in Water Formulation Used:

| INGREDIENTS %/wt | Example | | | |
|---|---|---|---|---|
| | 91 | 92 | 93 | 94 |
| Water | qs | qs | qs | qs |
| Disodium EDTA | 0.05 | 0.05 | 0.05 | 0.05 |
| Methyl Gluceth-20 | 5.00 | 5.00 | 5.00 | 5.00 |
| Ethylhexyl Stearate | 10.50 | 10.50 | 10.50 | 10.50 |
| Glyceryl Stearate/PEG 100 Stearate | 2.50 | 2.50 | 2.50 | 2.50 |
| PEG-20 METHYL GLUCOSE - SESQUISTEARATE | 3.00 | 3.00 | 3.00 | 3.00 |
| Cetearyl Alcohol | 3.00 | 3.00 | 3.00 | 3.00 |
| AVOBENZONE | 1.00 | 1.00 | 1.00 | 1.00 |
| Homosalate | 15.00 | 15.00 | 15.00 | 15.00 |
| Oxybenzone | 4.00 | 4.00 | 4.00 | 4.00 |
| Octisalate | 4.00 | 4.00 | 4.00 | 4.00 |
| Preservative | 1.00 | 1.00 | 1.00 | 1.00 |
| C20-C-40 Olivate | 3.00 | 0.00 | 3.00 | 0.00 |
| Synthetic Beeswax | 0.00 | 3.00 | 0.00 | 3.00 |
| Zinc Oxide | 2.00 | 2.00 | 0.00 | 0.00 |
| PVP Eicosene Copolymer | 0.75 | 0.75 | 0.75 | 0.75 |
| C10-C30 Alkyl Acrylate Crosspolymer | 1.00 | 1.00 | 1.00 | 1.00 |

Water-in-Oil Formulation Used

| INGREDIENTS %/wt | Example | | | |
|---|---|---|---|---|
| | 95 | 96 | 97 | 98 |
| Water | qs | qs | qs | qs |
| Disodium EDTA | 0.05 | 0.05 | 0.05 | 0.05 |
| Glycerin | 5.00 | 5.00 | 5.00 | 5.00 |
| Isopropyl Palmitate | 3.50 | 3.50 | 3.50 | 3.50 |
| Isopropyl Myristate | 4.00 | 4.00 | 4.00 | 4.00 |
| Glyceryl Stearate SE | 3.50 | 3.50 | 3.50 | 3.50 |
| Cetyl Alcohol | 2.00 | 2.00 | 2.00 | 2.00 |
| METHYL GLUCOSE SESQUISTEARATE | 1.00 | 1.00 | 1.00 | 1.00 |
| L-ascorbyl acetate | 1.00 | 1.00 | 1.00 | 1.00 |
| Preservative | 1.00 | 1.00 | 1.00 | 1.00 |
| Behenyl Olivate | 5.00 | 0.00 | 5.00 | 0.00 |
| Beeswax | 0.00 | 5.00 | 0.00 | 5.00 |
| Iron Oxides | 0.00 | 0.00 | 12.00 | 12.00 |
| Hydroxyethyl Cellulose | 0.75 | 0.75 | 0.75 | 0.75 |
| Carbomer 980 | 0.50 | 0.50 | 0.50 | 0.50 |

Oil Containing Cleanser

| INGREDIENTS %/wt | Example | | | |
|---|---|---|---|---|
| | 99 | 100 | 101 | 102 |
| Water | qs | qs | qs | qs |
| Disodium EDTA | 0.05 | 0.05 | 0.05 | 0.05 |
| Glycerin | 3.00 | 3.00 | 3.00 | 3.00 |
| Hydroxypropyl Methyl Cellulose | 0.75 | 0.75 | 0.75 | 0.75 |
| Refined Olive OIL | 6.50 | 6.50 | 6.50 | 6.50 |
| Sodium Cocoamphoacetate | 20.00 | 20.00 | 20.00 | 20.00 |
| Cocoa midopropyl Betain | 4.00 | 4.00 | 4.00 | 4.00 |
| Glyceryl Laurate | 1.00 | 1.00 | 1.00 | 1.00 |
| Sodium Laureth Sulfate | 38.00 | 38.00 | 0.00 | 0.00 |
| Myristic Acid | 5.20 | 5.20 | 5.20 | 5.20 |
| Preservative | 1.00 | 1.00 | 1.00 | 1.00 |
| Behenyl Olivate | 0.00 | 1.20 | 1.20 | 0.00 |
| Hydrogenated castor wax | 1.20 | 0.00 | 0.00 | 1.20 |

The unique emollient, condition and spread properties that differentiate these esters as per the Partition Coefficient definition is present with esters having a final melting point of 45 C and Higher. The Behenyl Olivate as an example provides the defined skin properties, but also is an effective oil thickening agent. Traditional oil thickening agents will not deliver the emollient, conditioning properties as stated with these esters. Our formulations measuring the feel and texture were compared against other thickening agents.

Anhydrous Stick Formulation:

| | Example | | | |
|---|---|---|---|---|
| | 103 | 104 | 105 | 106 |
| Castor Oil | qs | qs | qs | qs |
| Ethylhexyl Palmitate | 12.50 | 12.50 | 12.50 | 12.50 |
| Behenyl Olivate | 6.00 | 0.00 | 0.00 | 0.00 |
| Beeswax | 0.00 | 6.00 | 0.00 | 0.00 |
| Stearyl Olivate | 0.00 | 0.00 | 6.00 | 0.00 |
| Hydrogenated castor Wax | 0.00 | 0.00 | 0.00 | 6.00 |
| Iron Oxides | 12.00 | 12.00 | 12.00 | 12.00 |

Anhydrous Stick Formulation:

| | Example | | | |
|---|---|---|---|---|
| | 107 | 108 | 109 | 110 |
| Hydrogenated Castor Oil | qs | qs | qs | qs |
| Palm Kernel Oil | 12.50 | 12.50 | 12.50 | 12.50 |
| Behenyl Olivate | 6.00 | 0.00 | 0.00 | 0.00 |
| Beeswax | 0.00 | 6.00 | 0.00 | 0.00 |
| Stearyl Olivate | 0.00 | 0.00 | 6.00 | 0.00 |
| Hydrogenated castor Wax | 0.00 | 0.00 | 0.00 | 6.00 |
| Aluminum Chlorohydrate | 18.00 | 18.00 | 18.00 | 18.00 |

Qs in the above examples means "quantity sufficient" to equal 100%

Hair Conditioner(Added)

| | Example | | |
|---|---|---|---|
| | 111 | 112 | 113 |
| Cetearyl Alcohol, Ceteareth-20 | 2.50 | 2.50 | 2.50 |
| Steareth-21 | 1.50 | 1.50 | 1.50 |
| Cetyl Alcohol | 2.00 | 2.00 | 2.00 |
| Stearyl Olivate | 2.25 | 0.00 | 0.00 |
| Behenyl Olivate | 0.00 | 2.50 | 0.00 |
| Behenyl Safflowate | 0.00 | 0.00 | 2.50 |
| Isopropyl Palmitate | 1.50 | 1.50 | 1.50 |
| Hydrolyzed Wheat Protien | 1.00 | 1.00 | 1.00 |
| Propylene Glycol | 1.50 | 1.50 | 1.50 |
| D.I. Water | qs | qs | qs |
| Preservative | 1.00 | 1.00 | 1.00 |

Oil-in-Water Formulation Used Containing the Gels and Active Ingredients:

| | Example | | | |
|---|---|---|---|---|
| INGREDIENTS %/wt | 114 | 115 | 116 | 117 |
| Water | qs | qs | qs | qs |
| Disodium EDTA | 0.05 | 0.05 | 0.05 | 0.05 |
| C10-C30 Alkyl Acrylate Crosspolymer | 1.00 | 1.00 | 1.00 | 1.00 |
| Glycerin | 5.00 | 5.00 | 5.00 | 5.00 |
| GEL-O | 10.50 | | | |
| GEL-OS | | 10.50 | | |
| GEL-CO | | | 10.50 | |
| Gel-CS | | | | 10.50 |
| Glyceryl Stearate/PEG 100 Stearate | 2.50 | 2.50 | 2.50 | 2.50 |
| PEG-20 Methyl Glucose Sesquistearate | 3.00 | 3.00 | 3.00 | 3.00 |
| Cetearyl Alcohol | 3.00 | 3.00 | 3.00 | 3.00 |
| Homosalate | 8.00 | 8.00 | 8.00 | 8.00 |
| Oxybenzone | 4.00 | 4.00 | 4.00 | 4.00 |
| Octylsalate | | | | |
| Zinc Oxide | 2.00 | 2.00 | 2.00 | 2.00 |
| PVP Eicosene Coplymer | 0.75 | 0.75 | 0.75 | 0.75 |
| Preservative | 1.00 | 1.00 | 1.00 | 1.00 |

Gels defined as: Partition Coefficent esters(liquids: OctyldodecylOlivate (O), Octyldodecyl (OS)Safflowate, Cetyl Olivate (CO), Cetyl Safflowate (CS))

Oil-in-Water Formulation Used Containing the Gels and Pigment Ingredients:

| | Example | | | |
|---|---|---|---|---|
| INGREDIENTS %/wt | 118 | 119 | 120 | 121 |
| Water | qs | qs | qs | qs |
| Disodium EDTA | 0.05 | 0.05 | 0.05 | 0.05 |
| C10-C30 Alkyl Acrylate Crosspolymer | 1.00 | 1.00 | 1.00 | 1.00 |
| Methyl Gluceth-20 | 5.00 | 5.00 | 5.00 | 5.00 |
| GEL-O | 10.50 | | | |
| GEL-OS | | 10.50 | | |
| GEL-CO | | | 10.50 | |
| Gel-CS | | | | 10.50 |
| Glyceryl Stearate/PEG 100 Stearate | 2.50 | 2.50 | 2.50 | 2.50 |
| Cetearyl Alcohol/Cetearth-20 | 3.00 | 3.00 | 3.00 | 3.00 |
| Cetearyl Alcohol | 2.75 | 2.75 | 2.75 | 2.75 |
| Zinc Oxide | 2.00 | 2.00 | 2.00 | 2.00 |
| Iron Oxides/Pigments | 12.00 | 12.00 | 12.00 | 12.00 |
| Nylon | 3.00 | 3.00 | 3.00 | 3.00 |
| Boron Nitride | 0.75 | 0.75 | 0.75 | 0.75 |
| PVP Eicosene Coplymer | 0.75 | 0.75 | 0.75 | 0.75 |
| Preservative | 1.00 | 1.00 | 1.00 | 1.00 |

Gels defined as: Partition Coefficent esters(liquids: OctyldodecylOlivate (O), Octyldodecyl (OS)Safflowate, Cetyl Olivate (CO), Cetyl Safflowate (CS))

Water-in-Oil Using the Gel Compositions an Pigments

| | Example | | | |
|---|---|---|---|---|
| INGREDIENTS %/wt | 122 | 123 | 124 | 125 |
| Water | qs | qs | qs | qs |
| Disodium EDTA | 0.05 | 0.05 | 0.05 | 0.05 |
| C10-C30 Alkyl Acrylate Crosspolymer | 1.00 | 1.00 | 1.00 | 1.00 |
| Methyl Gluceth-10 | 1.00 | 1.00 | 1.00 | 1.00 |
| GEL-O | 14.50 | | | |
| GEL-OS | | 14.50 | | |
| GEL-CO | | | 14.50 | |
| Gel-CS | | | | 14.50 |
| Glyceryl Stearate SE | 3.50 | 3.50 | 3.50 | 3.50 |
| Cetearyl Alcohol | 2.75 | 2.75 | 2.75 | 2.75 |
| Methyl Glucose Sequistearate | 1.50 | 1.50 | 1.50 | 1.50 |
| Zinc Oxide | 2.00 | 2.00 | 2.00 | 2.00 |
| Iron Oxides/Pigments | 12.00 | 12.00 | 12.00 | 12.00 |
| Nylon | 3.00 | 3.00 | 3.00 | 3.00 |
| Boron Nitride | 0.75 | 0.75 | 0.75 | 0.75 |
| PVP Eicosene Coplymer | 0.75 | 0.75 | 0.75 | 0.75 |
| Preservative | 1.00 | 1.00 | 1.00 | 1.00 |

Gels defined as: Partition Coefficent esters(liquids: OctyldodecylOlivate (O), Octyldodecyl (OS)Safflowate, Cetyl Olivate (CO), Cetyl Safflowate (CS))

Anhydrous Stick Formulation:Containing the Gel Compositions
Ingredients %/Wt

| | Example | | | |
|---|---|---|---|---|
| | 126 | 127 | 128 | 129 |
| Castor Oil | qs | qs | | |
| GEL-O | 14.50 | | | |

-continued

| | Example | | | |
|---|---|---|---|---|
| | 126 | 127 | 128 | 129 |
| GEL-OS | | 14.50 | | |
| GEL-CO | | | 14.50 | |
| GEL-CS | | | | 14.50 |
| Beeswax | 6.00 | 6.00 | 6.00 | 6.00 |
| Carnauba Wax | 3.00 | 3.00 | 3.00 | 3.00 |
| Candelilla Wax | 7.00 | 7.00 | 7.00 | 7.00 |
| Ozokerite Wax | 4.00 | 4.00 | 4.00 | 4.00 |
| Iron Oxides | 12.00 | 12.00 | 12.00 | 12.00 |

Gels defined as : Partition Coefficent esters(liquids: OctyldodecylOlivate (O), Octyldodecyl (OS)Safflowate, Cetyl Olivate (CO), Cetyl Safflowate (CS))

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

The invention claimed is:

1. A composition consisting of an ester made by the trans-esterification reaction of;
   (a) a fatty alcohol, having a melting point of between 35° C. and 75° C.;
   (b) with a triglyceride having a iodine value of between 75 and 195 mg KOH/gm and
   (c) optionally a catalyst,
   forming a mixture of unreacted triglyceride, monoglyceride, diglyceride, glycerin and unsaturated ester of the triglyceride reacted with the fatty alcohol;
   said trans-esterification conducted at as temperature of 150-200° C. for 4 to 10 hours;
   said composition is allowed to cool without agitation to 25° C., over a period of at least 30 minutes,
   whereupon a top solid layer forms and a bottom liquid layer forms;
   finally, the bottom layer is removed.

2. The ester composition of claim 1 wherein the fatty alcohol has a melt point of between 40° C. and 60° C.

3. The ester composition of claim 1 wherein the fatty alcohol has a melt point of between 35° C. and 50° C.

4. The ester composition of claim 1 wherein the fatty alcohol has a melt point of between 50° C. and 75° C.

5. The ester composition of claim 1 wherein the iodine value of the triglyceride ranges from 85-95 mg KOH/gm.

6. The ester composition of claim 1 wherein the iodine value of the triglyceride ranges from 100-125 mg KOH/gm.

7. The ester composition of claim 1 wherein the reaction is conducted with no catalyst.

8. The ester composition of claim 1 wherein the reaction is conducted with between around 0.1 and 0.3% by weight stannous oxylate.

9. The ester composition of claim 1 wherein said trans-esterification is conducted at as temperature of 150-170° C. for 4 to 10 hours.

10. The ester composition of claim 1 wherein said trans-esterification is conducted at as temperature of 150-170° C. for 7 to 10 hours.

11. The ester composition of claim 1 wherein the composition is allowed to cool without agitation to 25° C., over a period of at least 60 minutes.

12. A process for conditioning skin, which comprises contacting the skin with an effective conditioning concentration of a composition consisting of an ester made by the trans-esterification reaction of;
   (a) a fatty alcohol, having a melting point of between 35° C. and 75° C.;
   (b) with a triglyceride having a iodine value of between 75 and 195 mg KOH/gm and
   (c) optionally a catalyst,
   forming a mixture of unreacted triglyceride, monoglyceride, diglyceride, glycerin and unsaturated ester of the triglyceride reacted with the self fatty alcohol;
   said trans-esterification conducted at as temperature of 150-200° C. for 4 to 10 hours;
   said composition is allowed to cool without agitation to 25° C., over a period of at least 30 minutes,
   whereupon a top solid layer forms and a bottom liquid layer forms;
   finally, the bottom layer is removed from the mixture by resulting in a lipophillic composition of the present invention.

13. The process of claim 12 wherein, the effective conditioning concentration ranges from 0.1% to 25% by weight.

14. The process of claim 12 wherein the effective conditioning concentration ranges from 1% to 20% by weight.

15. The process of claim 12 wherein the effective conditioning concentration ranges from 10% to 15% by weight.

16. An ester composition consisting of
   (a) between 1-5% by weight of;

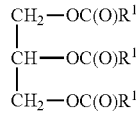

(b) between 1-10% by weight of;

(c) between 0-5% by weight of a mixture of monoglycerides conforming to the following structure:

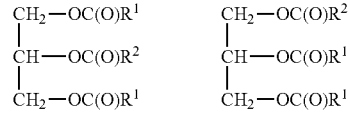

(d) between 5-15% by weight of a mixture of diglycerides conforming to the following structure:

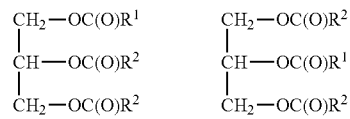

between 60-89% by weigh an ester conforming to the following structure;

and between 0-5% by weight of glycerin conforming to the following structure:
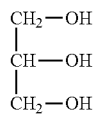
wherein
R$^1$ is at least 50% by weight C18 unsaturated selected from the group consisting of oleyl and linoleyl;
R$^2$ is saturated alkyl having 13 to 23 carbon atoms.
* * * * *